United States Patent
Liu et al.

(10) Patent No.: US 12,159,357 B2
(45) Date of Patent: Dec. 3, 2024

(54) AR-BASED METHOD AND SYSTEM FOR MONITORING SAFETY OF CARBON DIOXIDE INCUBATOR

(71) Applicant: China Academy of Art, Hangzhou (CN)

(72) Inventors: Zheng Liu, Hangzhou (CN); Zhixiang Zhao, Hangzhou (CN)

(73) Assignee: China Academy of Art, Hangzhou (CN)

( * ) Notice: Subject to any disclaimer, the term of this patent is extended or adjusted under 35 U.S.C. 154(b) by 199 days.

(21) Appl. No.: 18/051,400

(22) Filed: Oct. 31, 2022

(65) Prior Publication Data
US 2024/0071005 A1    Feb. 29, 2024

(30) Foreign Application Priority Data
Aug. 24, 2022 (CN) .......................... 202211019525.0

(51) Int. Cl.
G06T 19/00    (2011.01)
C12M 1/00    (2006.01)
G06F 30/20    (2020.01)
G06T 7/33    (2017.01)

(52) U.S. Cl.
CPC ........... *G06T 19/006* (2013.01); *C12M 41/14* (2013.01); *G06F 30/20* (2020.01); *G06T 7/33* (2017.01)

(58) Field of Classification Search
None
See application file for complete search history.

(56) References Cited

PUBLICATIONS

Gunnarsson et al., "Visualisation of Sensor Data Using Handheld Augmented Reality", 2006. (Year: 2006).*

* cited by examiner

*Primary Examiner* — Nicholas R Wilson
(74) *Attorney, Agent, or Firm* — Schwegman Lundberg & Woessner, P.A.

(57) ABSTRACT

An AR-based method and system for monitoring safety of a carbon dioxide incubator are provided. The method includes obtaining temperature data, carbon dioxide concentration data and door and window opening and closing data through sensors; collecting image information of the carbon dioxide incubator and establishing a virtual space coordinate system; constructing a real space coordinate system according to a position of a camera, and acquiring a matrix of the carbon dioxide incubator in the real space coordinate system; transforming the matrix corresponding to the carbon dioxide incubator image in the real coordinate system into a matrix in the virtual coordinate system according to a transformation relation matrix, so as to construct position and pose data of a virtual incubator; and determining a risk grade according to the position and pose data of the virtual incubator and collected sensor data, and visualizing and displaying risk in an augmented-reality manner.

9 Claims, 4 Drawing Sheets providing a temperature sensor, a carbon dioxide sensor and a door and window sensor in a carbon dioxide incubator, and obtaining temperature data, carbon dioxide concentration data and door and window opening and closing data through these sensors;

collecting image information of the carbon dioxide incubator and establishing a virtual space coordinate system;

constructing a real space coordinate system according to a position of a camera, and acquiring a matrix of the carbon dioxide incubator in the real space coordinate system;

transforming the matrix corresponding to the carbon dioxide incubator image in the real coordinate system into a matrix in the virtual coordinate system according to a transformation relation matrix, so as to construct position and pose data of a virtual incubator;

determining a risk grade according to the position and pose data of the virtual incubator and collected sensor data, and visualizing and displaying risk in an augmented-reality manner.

AR-BASED METHOD AND SYSTEM FOR MONITORING SAFETY OF CARBON DIOXIDE INCUBATOR

CROSS REFERENCE TO RELATED APPLICATION

This Non-provisional application claims priority under 35 U.S.C. § 119(a) to Chinese Patent Application No. 202211019525.0, filed on 24 Aug. 2022, the entire contents of which is hereby incorporated by reference in its entirety.

TECHNICAL FIELD

The disclosure relates to the technical field of carbon dioxide monitoring, in particular to an AR-based method and system for monitoring safety of a carbon dioxide incubator.

BACKGROUND ART

At present, carbon dioxide incubators are increasingly more favored by various laboratories. In order to ensure smooth progress of research works, cultivation equipment in the laboratories needs to stably control a temperature, a carbon dioxide concentration and humidity, and at the same time ensure that cultivated samples are not contaminated by microorganisms. Therefore, effective monitoring of microclimate environment inside the carbon dioxide incubators is a prerequisite for smooth progress of culture experiments. The carbon dioxide incubators are widely used in research and production of medicine, immunology, microbiology and other fields. Therefore, the carbon dioxide incubators are usually used to cultivate various microorganisms such as cells and viruses, but these microorganisms themselves have strong toxicity, and once a biosafety accident occurs, consequences are unimaginable, and thus the biosafety of the incubators is very important.

A monitoring system for a traditional carbon dioxide incubator mainly provides a number prompt, and only displays various environmental variables (such as temperature, humidity, gas concentration, etc.) separately, and does not grade and handle experimental safety problems of the incubator, and thus experimenters can't control and evaluate experimental safety accidents well. Meanwhile, a single number prompt can't exhibit continuous change of an environmental variable in a certain period of time in the carbon dioxide incubator. Therefore, the monitoring system for the traditional carbon dioxide incubator still has many shortcomings, and safety monitoring and early warning ability needs to be further improved.

SUMMARY

One of objects of the present disclosure is to provide an AR-based method and system for monitoring safety of a carbon dioxide incubator. In the method and system, AR technology and various sensors including a carbon dioxide sensor are utilized, and alarm information is visualized and continuously displayed over time through colorless and odorless carbon dioxide concentration information collected by the carbon dioxide sensor and the AR technology, thus improving monitored safety of the carbon dioxide incubator.

Another object of the present disclosure is to provide an AR-based method and system for monitoring safety of a carbon dioxide incubator. In the method and system, a graded early warning method is established, and different grades of safety risks are comprehensively obtained by using a carbon dioxide sensor, a temperature sensor and image-based posture detection, so as to improve monitoring accuracy of the carbon dioxide incubator.

Another object of the present disclosure is to provide an AR-based method and system for monitoring safety of a carbon dioxide incubator. In the method and system, a virtual component is constructed through AR technology, and data detected by various sensors and detection devices is combined to construct a virtual display interface at a display end, and then clear visual display can be realized by means of a thermal diagram.

In order to achieve at least one of above objects, an AR-based method for monitoring safety of a carbon dioxide incubator is further provided in the present disclosure, which includes:

providing a temperature sensor, a carbon dioxide sensor and a door and window sensor in a carbon dioxide incubator, and obtaining temperature data, carbon dioxide concentration data and door and window opening and closing data through these sensors;

collecting image information of the carbon dioxide incubator and establishing a virtual space coordinate system;

constructing a real space coordinate system according to a position of a camera, and acquiring a matrix of the carbon dioxide incubator in the real space coordinate system;

transforming the matrix corresponding to the carbon dioxide incubator image in the real coordinate system into a matrix in the virtual coordinate system according to a transformation relation matrix, so as to construct position and pose data of a virtual incubator; and determining a risk grade according to the position and pose data of the virtual incubator and collected sensor data, and visualizing and displaying risk in an augmented-reality manner.

According to one of the preferred embodiments of the disclosure, after the temperature data, the carbon dioxide concentration data and the door and window opening and closing data obtained by the temperature sensor, the carbon dioxide sensor and the door and window sensor are collected, a current risk grade of the carbon dioxide incubator is further determined. With an abnormal condition for respective sensor data being set, risk alarm information is output when an abnormal condition of at least one sensor data is met.

According to another preferred embodiment of the present disclosure, a method for determining the risk grade includes: obtaining the sensor data including the temperature data, the carbon dioxide concentration data and the door and window opening and closing data; if any one of the sensor data is abnormal data, outputting third-grade risk warning information, if any two of the sensor data are abnormal data, outputting second-grade alarm information; and if all of three sensors have abnormal data, outputting first-grade alarm information.

According to another preferred embodiment of the present disclosure, the door and window sensor can be a reed switch magnetic door and window sensor. The reed switch magnetic door and window sensor is installed at an edge of a door frame of the carbon dioxide incubator, and is configured for sensing a closed state between a door body and a frame of the carbon dioxide incubator. If an induction circuit inside the reed switch magnetic door and window sensor is in an open state, it is determined that the door frame of the carbon dioxide incubator is currently in an open state;

otherwise, it is determined that the door frame of the carbon dioxide incubator is currently in an closed state.

According to another preferred embodiment of the present disclosure, a method for visualizing the risk grade includes: collecting all of current sensor data, and transmitting all of the current sensor data to an Internet of Things data platform by using a KEPServer module. The Internet of Things platform defines an interface, and a predefined interface is called through a 3D rendering platform and JSON format data is used for interaction. After obtaining the JSON format data, the 3D rendering platform analyzes the JSON format data to obtain the sensor data, and executes different rendering pages according to a risk determination result.

According to another preferred embodiment of the present disclosure, a method for constructing the matrix of the carbon dioxide incubator in the real coordinate system includes: configuring a plurality of markers on the carbon dioxide incubator; installing a camera, the installed camera being capable of identifying all of configured markers; setting a coordinate system from camera's perspective; and calculating coordinates of all markers under a coordinate system from camera's perspective, for tracking a position of the carbon dioxide incubator with the markers.

According to another preferred embodiment of the present disclosure, a method for constructing a matrix of the carbon dioxide incubator in a virtual coordinate system includes: rendering a template image, setting virtual marker information on the template image, establishing a virtual space coordinate system according to the rendered template image, and calculating marker coordinates in a virtual template image according to the virtual space coordinate system.

According to another preferred embodiment of the present disclosure, a method for transforming a matrix in the real space coordinate system into a matrix in the virtual coordinate system includes: identifying identification information of a virtual template image, taking the identification information as a feature point, performing feature comparison between the feature point and identification information in the real space coordinate system, obtaining a matrix in the real coordinate system of the matched identification information in real coordinate system, calculating a coordinate system transformation matrix after the feature comparison, and combining a real image of the carbon dioxide incubator with the virtual template image according to the transformation matrix.

In order to achieve at least one of the above objects, an AR-based system for monitoring safety of a carbon dioxide incubator is further provided in the present disclosure, which executes an AR-based method for monitoring safety of a carbon dioxide incubator described above.

The present disclosure further provides a computer-readable storage medium with a computer program stored therein, and the computer program can be executed by a processor to implement the AR-based method for monitoring safety of a carbon dioxide incubator described above.

DETAILED DESCRIPTION

The following description is intended to disclose the present invention so as to enable those skilled in the art to implement the invention. The embodiments in the following description are by way of example only, and other obvious variations will occur to those skilled in the art. The basic principle of the invention defined in the following description can be applied to other implementations, modified, improved and equivalent schemes and other schemes without departing from the spirit and scope of the utility model.

It can be understood that the term "a or an" should be understood as "at least one" or "one or more", that is, in one embodiment, the number of an element may be one, while in other embodiments, the number of the element may be multiple, and the term "an" cannot be understood as limiting the number.

Figure 1:
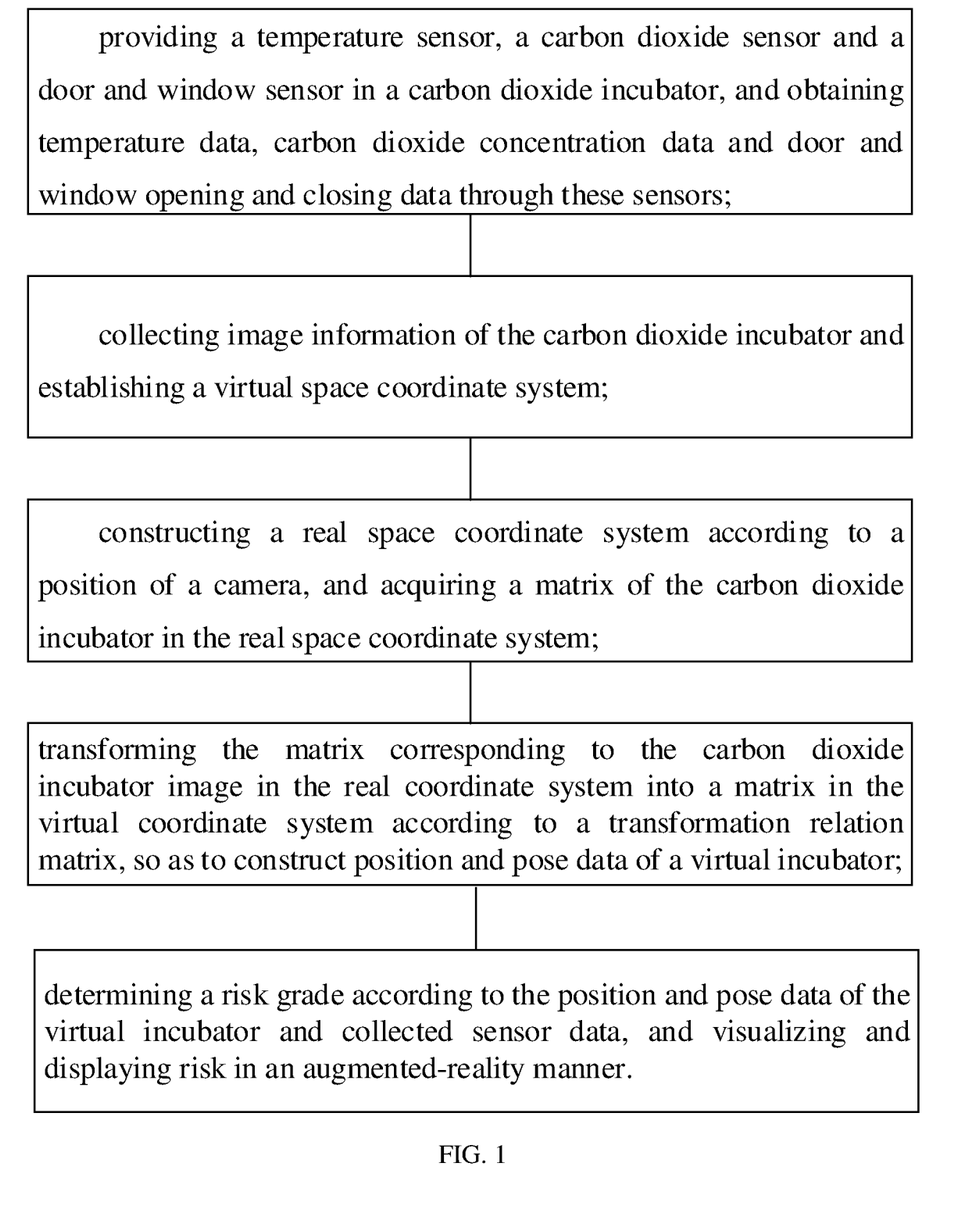
FIG. 1 shows a flow chart of an AR-based method for monitoring safety of a carbon dioxide incubator according to the present disclosure.
Figure 2:
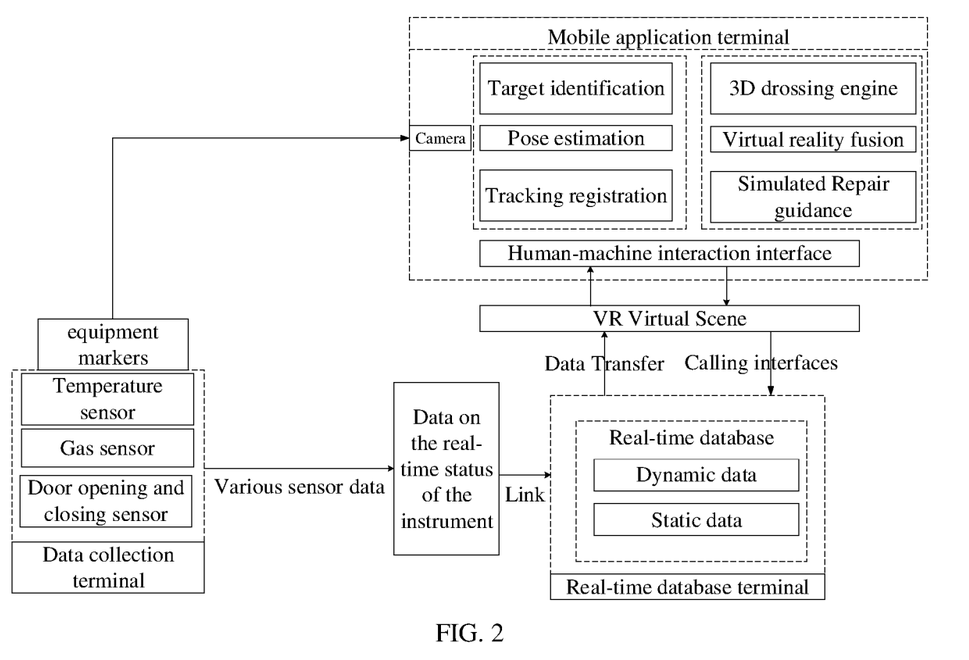
FIG. 2 shows a structural schematic diagram of an AR-based system for monitoring safety of a carbon dioxide incubator according to the present disclosure.
Figure 3:
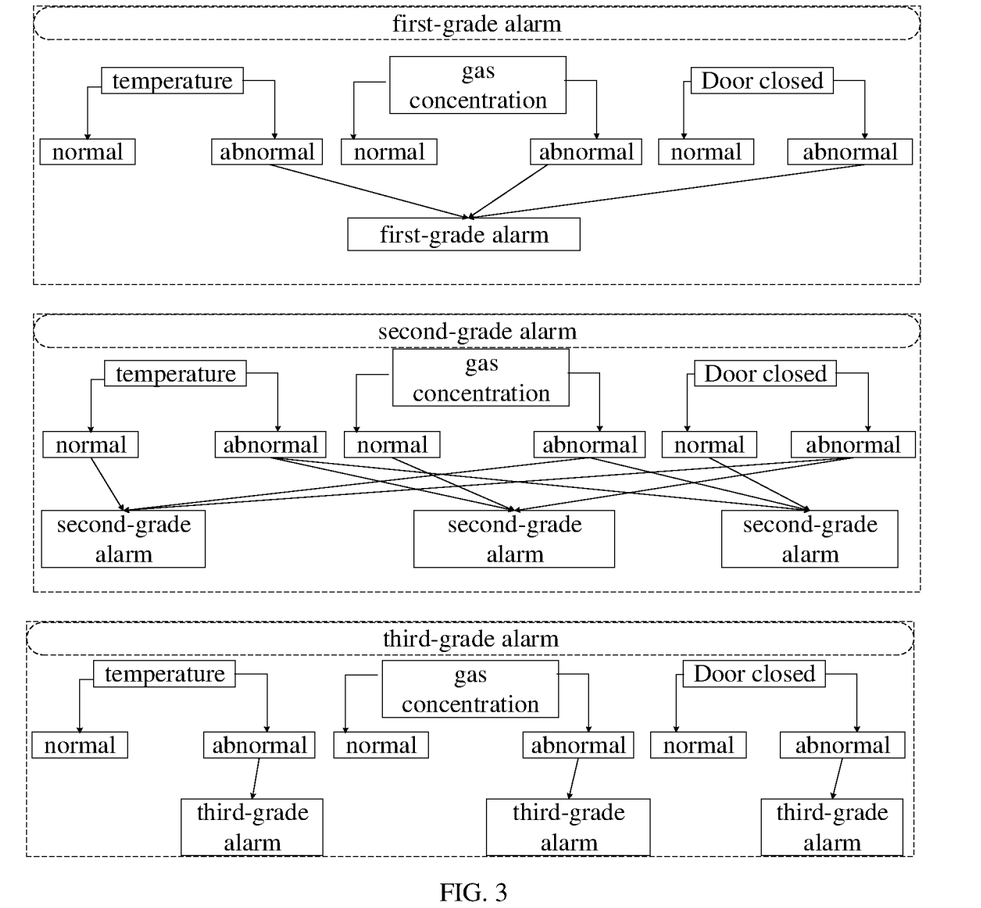
FIG. 3 shows a schematic diagram of different early warning states of the carbon dioxide incubator according to the present disclosure.

With reference to FIGS. 1 to 3, an AR-based method and system for monitoring safety of a carbon dioxide incubator are provided in this disclosure. The method includes: firstly installing different types of sensors in the carbon dioxide incubator. The sensors include a temperature sensor for sensing a temperature of the carbon dioxide incubator, and a carbon dioxide sensor for sensing a carbon dioxide concentration in the carbon dioxide incubator, and a door and window sensor for sensing opening and closing conditions of doors and windows. Further, in one of the preferred embodiments of the present disclosure, a data acquisition card is configured, which is connected with the carbon dioxide incubator and monitors a running state of the carbon dioxide incubator. The method further includes constructing a template image by using AR technology, and configuring conditions for different risk grades; after obtaining data of various sensors, determining whether corresponding grade requirement is met according to preset risk grade conditions; if the corresponding grade requirement is met, rendering a corresponding template and constructing an AR template image and the real image of the carbon dioxide incubator which are matched and fused with each other, which are visualized and displayed on the terminal.

Specifically, in one of the preferred embodiments of the present disclosure, the system includes a wireless transmission module. The wireless transmission module is configured to transmit sensor data to an upper computer. In this embodiment, the wireless transmission module can be set as a Bluetooth module or a WiFi module, and the carbon dioxide sensor is installed inside the carbon dioxide incubator to collect carbon dioxide concentration information inside the carbon dioxide incubator in real time. The temperature sensor is also installed inside the carbon dioxide incubator and is configured for collecting real-time temperature data inside the carbon dioxide incubator in real time. The door and window sensor is installed on a door frame of the carbon dioxide incubator, and is configured to determine whether the door and window is closed by sensing whether there is contact between a door body and the door frame.

The system includes a data acquisition terminal, a storage database and a mobile terminal as a whole. The data acquisition terminal includes a temperature sensor, a carbon dioxide sensor, a door and window sensor, and a front-end server, a data acquisition card and a wireless communication module which are installed in advance. After the front-end server acquires data of various sensors through the data acquisition card, the front-end server transmits the acquired data to the storage database for storage, and the wireless transmission module transmits corresponding sensor data to an upper computer or a mobile terminal in real time or at a specified period of time.

Specifically, in one of the preferred embodiments of the present disclosure, the carbon dioxide sensor is preferably an MH-Z16 carbon dioxide sensor. The MH-Z16 carbon dioxide sensor is installed inside the carbon dioxide incubator and is configured for detecting carbon dioxide concentration information and transmitting the detected carbon dioxide concentration information to the front-end server. In one of the preferred embodiments of the present disclosure, the temperature sensor adopts a DHT11 temperature and humidity sensor. The DHT11 temperature and humidity sensor is installed in the carbon dioxide incubator and is configured for collecting temperature information inside the carbon dioxide incubator in real time and transmit a temperature information detection result to the front-end server. In one of the preferred embodiments of the present disclosure, the door and window sensor is a reed switch magnetic door and window sensor. The reed switch magnetic door and window sensor is installed on the door body and the door frame of the carbon dioxide incubator. The reed switch magnetic door and window sensor has a detection circuit therein. When the door body and the door frame of the carbon dioxide incubator are not closed, due to the door body and the door frame being in an open state at this time, the detection circuit inside the reed switch magnetic door and window sensor is in an open state because the sensors corresponding to the door body and the door frame do not function in sensing. When the door body and the door frame are in a closed state, because door and window closing information is detected inside the reed switch magnetic door and window sensor, the detection circuit inside the reed switch magnetic door and window sensor is in a conducting state due to induction of the sensors corresponding to the door body and the door frame, and the door and window are detected in a closed state at this time. The reed switch magnetic door and window sensor transmits the detected door and window opening and closing information to the front-end server.

Risk grade conditions are preset by the front-end server, and when the front-end server acquires data of the temperature sensor, the carbon dioxide sensor and the door and window sensor, the front-end server calculates whether the sensor data matches a corresponding risk grade, and if the sensor data matches the corresponding risk grade, the front-end server outputs the corresponding risk grade. In one of the preferred embodiments of the disclosure, the risk grades are preset to be three, namely third-grade alarm information, second-grade alarm information and first-grade alarm information. Data within a normal range of the temperature data, a normal range of carbon dioxide concentration and data regarding closing of the door and window are preset as normal data. For example, for the temperature data, a range of 0° to 40° can be configured as a normal temperature range according to laboratory requirements, and other temperature ranges are abnormal. Accordingly, a normal range of carbon dioxide concentration in the carbon dioxide incubator can be configured according to experimental requirement, and a specific value of the normal range is not specifically limited in this embodiment. After normal ranges for temperature detection and carbon dioxide concentration detection are preset, current real-time carbon dioxide concentration data and temperature data detected by the carbon dioxide sensor and the temperature sensor, and the door and window opening and closing data of the carbon dioxide incubator obtained by the door and window sensor are further calculated. If there is abnormality for any of currently detected real-time sensor data, the preset risk grade conditions are searched to match the third-grade alarm information, and a rendered third-grade alarm information template image fused with the real image of the carbon dioxide incubator can be displayed on a page of mobile terminal. If there is abnormality for any two of the currently detected real-time sensor data, the preset risk grade conditions are searched to match the second-grade alarm information, and a rendered second-grade alarm information template image fused with the real image of the carbon dioxide incubator can be further displayed on the page of the mobile terminal according to the second-grade alarm information. If there is abnormality for three of the currently detected real-time sensor data, the preset risk grade conditions are searched to match the first-grade alarm information, and a rendered first-grade alarm information template image fused with the real image of the carbon dioxide incubator can be further displayed on the page of the mobile terminal according to the first-grade alarm information. The fused images are further transmitted to the mobile terminal for display.

In detail, alarm information for different risk grades is displayed in different ways on the mobile terminal. For example, if the mobile terminal receives the third-level alarm information, the virtual template image displayed and rendered on the page of the mobile terminal includes an image with characters "third-grade alarm", and the characters "third-grade alarm" can be configured as a yellow flashing image, so that a current risk grade of the carbon dioxide incubator can be quickly and intuitively visualized and displayed on the mobile terminal. If the mobile terminal receives the second-level alarm information, the virtual template image displayed and rendered on the page of the mobile terminal includes an image with characters "second-grade alarm", and the characters "second-grade alarm" can be configured as an orange flashing image. If the mobile terminal receives the first-level alarm information, the virtual template image displayed and rendered on the page of the mobile terminal includes an image with characters "first-grade alarm", and the characters "first-grade alarm" can be configured as a red flashing image.

In a preferred embodiment of the present disclosure, A Unity3D platform is used as the rendering platform of the AR technology, the data acquisition card is preferably a RFID data acquisition card, the wireless communication module is preferably an ESP8266 WIFI module, and the storage database in the present disclosure adopts an OPC server to realize real-time transmission of stored data. In this embodiment, a KEPServer module is used to connect the storage database with the Internet of Things platform. The Internet of Things platform includes but is not limited to a Thingworx platform, and the KEPServer module is a kind of server software, and the KEPServer module can provide an OPC interface, and calling of a specified interface can be realized through the predefined OPC interface. The Thingworx platform is communicatively connected with the Unity3D platform, and the Unity3D platform can obtain the detected sensor data from the Thingworx platform in real time by calling the predefined OPC interface, and further package the sensor data into JSON format data through the called OPC interface, and call the OPC interface in the Unity3D platform to obtain the corresponding JSON format data. After the JSON format data is obtained, the JSON format data is further split and analyzed so as to obtain the sensor data. A predefined data transmission interface is obtained with a parameter GetServerUrl, and a calling frequency is set by a parameter 0.09 f. A high calling frequency of the data transmission interface may cause the server to crash, and the database cannot be refreshed. If the calling frequency is too low, some data may be lost, and at this time it is necessary to configure a calling frequency of 10 times per second.

Figure 4:
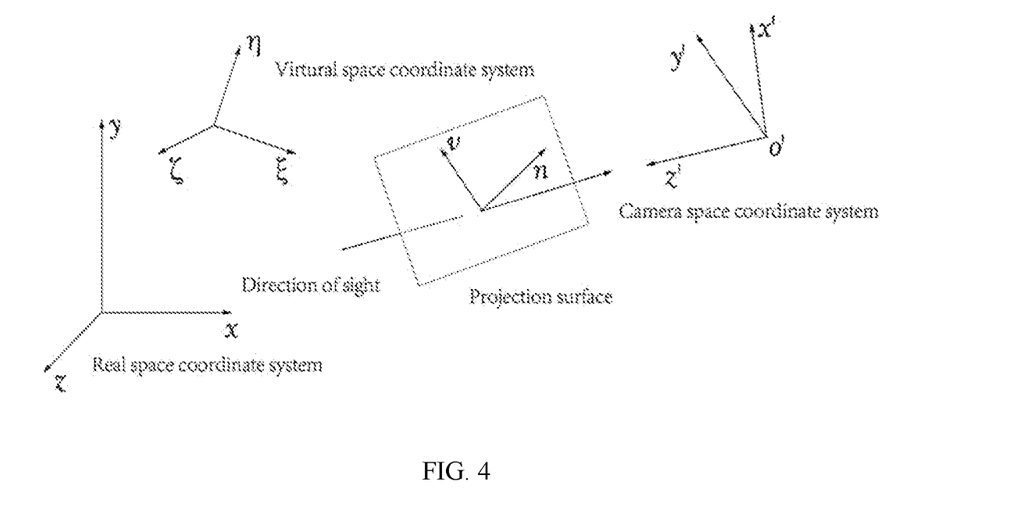
FIG. 4 shows a schematic diagram of respective coordinate system transformation under 3D registration technology according to the present disclosure.

It is worth mentioning that, in a preferred embodiment of the present disclosure, a marker is configured on the carbon dioxide incubator, and a collected image is identified and tracked according to the marker, so as to record a position and pose of the carbon dioxide incubator, and the image of the carbon dioxide incubator in the real-world coordinate system is further fused with the template image in the virtual coordinate system, so as to obtain a fused image that can objectively and clearly reflect a current state of the carbon dioxide incubator. Specifically, in this embodiment, the camera is used to identify the marker in the real world, and Vuforia SDK is used to calculate a $C_{4\times 4}$ matrix. A marker tracking module is adopted to realize technical effect of identification and tracking of the marker. The position and pose of the camera relative to the real-world coordinate system is calculated by the marker tracking module through the 3D registration technology to ensure a correct matching relationship, and the virtual template image can be displayed at a correct position on the mobile terminal in real time through matrix transformation between the real-world coordinate system and the virtual space coordinate system.

The virtual space coordinate system is transformed to the real space coordinate system by using a transformation relation matrix. The transformation using the transformation relation matrix is as follows:

$$\begin{bmatrix} x \\ y \\ z \\ 1 \end{bmatrix} = V_{4\times 4} \begin{bmatrix} \xi \\ \eta \\ \varsigma \\ 1 \end{bmatrix};$$

where $V_{4\times 4}$ is the transformation relation matrix, and x, y and z are transformed values in the real coordinate system, where $\xi$, $\eta$ and $\zeta$ respectively represent coordinates in the virtual world coordinate system. Because the coordinates in the virtual world coordinate system are preset as required, they are known matrices.

In this disclosure, a transformation mode from the real coordinate system to the camera's space coordinate system can be further calculated, so that a position and pose of the camera relative to the real world can be determined. A feature point of a video stream is acquired by the camera and is matched so as to obtain a transformation relationship, which is expressed with a second matrix:

$$\begin{bmatrix} x' \\ y' \\ z' \\ 1 \end{bmatrix} = \begin{bmatrix} R & T \\ 0 & 1 \end{bmatrix} \begin{bmatrix} x \\ y \\ z \\ 1 \end{bmatrix} = C_{4\times 4} \begin{bmatrix} x \\ y \\ z \\ 1 \end{bmatrix}$$

where parameters R and T are determined by the position and pose of the camera relative to the real-world coordinate system, and need to be measured in real time, where x, y and z in the second matrix respectively represent coordinates in the real-world coordinate system, and x', y' and z' respectively represent transformed coordinates in a camera coordinate system.

After obtaining the transformation relation matrix, coordinates in the camera interface coordinate system and coordinates in the real-world coordinate system, coordinates of the marker are transformed by the transformation relation matrix, and the feature point of the template image is matched in the camera coordinate system. If there's a same marker, the matched template image is output to the mobile terminal, and video data in which the template image matched with the feature point and the real image which are fused with each other are further displayed on the mobile terminal. Real-time data and information of the equipment can be obtained by an image rendering and display output module of the mobile terminal through the received JSON data, and then a virtual display interface is added in the AR display scene by establishing a UI component in Unity3D. In the disclosure, display on the mobile terminal can be made at the mobile terminal in a form of heat map according to obtained data such as temperature data and carbon dioxide concentration data.

Particularly, according to embodiments of the present disclosure, the process described above with reference to the flowchart may be implemented as a computer software program. For example, an embodiment of the present disclosure includes a computer program product including a computer program carried on a computer readable medium, and the computer program contains program code for executing the method shown in the flowchart. In such an embodiment, the computer program can be downloaded and installed from the network through a communication part, and/or installed from a removable medium. When the computer program is executed by a central processing unit (CPU), the above functions defined in the method of the present application are performed. It should be noted that the above-mentioned computer-readable medium in this application can be a computer-readable signal medium or a computer-readable storage medium or any combination of the above two. The computer-readable storage medium can be, for example, but not limited to, an electronic, magnetic, optical, electromagnetic, infrared, or semiconductor system, apparatus, or device, or any combination of the above. More specific examples of the computer-readable storage media may include, but are not limited to, electrical connections with one or more wire segments, portable computer disks, hard disks, random access memories (RAM), read-only memories (ROM), erasable programmable read-only memories (EPROM or flash memories), optical fibers, portable compact disk read-only memories (CD-ROMs), optical storage devices, magnetic storage devices, or any suitable combination of the above. In this application, the computer-readable storage medium can be any tangible medium containing or storing a program, which can be used by or in combination with an instruction execution system, apparatus or device. In this application, the computer-readable signal medium may include a data signal propagated in baseband or as a part of a carrier wave in which the computer-readable program code is carried. This propagated data signal can take various forms, including but not limited to an electromagnetic signal, an optical signal or any suitable combination of the above. A computer-readable signal medium can also be any computer-readable medium other than a computer-readable storage medium, which can send, propagate or transmit a program for use by or in connection with an instruction execution system, apparatus or device. The program code contained in the computer readable medium can be transmitted with any suitable medium, including but not limited to a wireless segment, an electric wire segment, a fiber optic cable, RF, etc., or any suitable combination of the above.

The flowcharts and block diagrams in the drawings illustrate the architecture, functions and operations of possible implementations of systems, methods and computer program products according to various embodiments of the present invention. In this regard, each block in the flowchart or block diagram may represent a module, a program segment or a part of code containing one or more executable instructions for implementing specified logical functions. It should also be noted that in some alternative implementations, the functions noted in the blocks may also occur in a different order from that noted in the drawings. For example, two blocks in succession may actually be executed in substantially parallel, or they may sometimes be executed in a reverse order, depending on the functions involved. It should also be noted that each block in the block diagrams and/or flowcharts, along with combinations of blocks in the block diagrams and/or flowcharts, can be implemented with dedicated hardware-based systems that perform specified functions or operations, or can be implemented with combinations of dedicated hardware and computer instructions.

It should be understood by those skilled in the art that the embodiments of the present invention described above and shown in the drawings are only taken as examples and do not limit the present invention; the function and structural principle of the invention have been shown and explained in the embodiments; any variation and modification can be made to the embodiments of the invention without departing from the principle.

What is claimed is:

1. An augmented reality based method for monitoring safety of a carbon dioxide incubator, comprising:
providing a temperature sensor, a carbon dioxide sensor and a door and window sensor in the carbon dioxide incubator, and obtaining a temperature data, a carbon dioxide concentration data and a door and window opening and closing data through the temperature sensor, the carbon dioxide sensor and the door and window sensor;
collecting an image information of the carbon dioxide incubator and establishing a virtual space coordinate system;
constructing a real space coordinate system according to a position of a camera, and acquiring a matrix of the carbon dioxide incubator in the real space coordinate system;
transforming the matrix corresponding to the carbon dioxide incubator image in the real coordinate system into a matrix in the virtual coordinate system according to a transformation relation matrix, so as to construct position and pose data of a virtual incubator; and
determining a risk grade according to the position and pose data of the virtual incubator and collected sensor data, and visualizing and displaying risk in an augmented-reality manner.

2. The augmented reality based method for monitoring safety of the carbon dioxide incubator according to claim 1, wherein after the temperature data, the carbon dioxide concentration data and the door and window opening and closing data obtained by the temperature sensor, the carbon dioxide sensor and the door and window sensor are collected, a current risk grade of the carbon dioxide incubator is further determined; and with an abnormal condition for respective sensor data being set, a risk alarm information is output when an abnormal condition of at least one sensor data is met.

3. The augmented reality based method for monitoring safety of the carbon dioxide incubator according to claim 1, wherein the method for determining the risk grade comprises: obtaining the sensor data comprising the temperature data, the carbon dioxide concentration data and the door and window opening and closing data; if any one of the sensor data is abnormal data, outputting third-grade risk warning information; if any two of the sensor data are abnormal data, outputting second-grade alarm information; and if all of the temperature data, the carbon dioxide concentration data and the door and window opening and closing data have abnormal data, outputting first-grade alarm information.

4. The augmented reality based method for monitoring safety of the carbon dioxide incubator according to claim 1, wherein the door and window sensor is a reed switch magnetic door and window sensor, the reed switch magnetic door and window sensor is installed at an edge of a door frame of the carbon dioxide incubator, and is configured for sensing a closed state between a door body and a frame of the carbon dioxide incubator; and if an induction circuit inside the reed switch magnetic door and window sensor is in an open state, it is determined that the door frame of the carbon dioxide incubator is currently in an open state; otherwise, it is determined that the door frame of the carbon dioxide incubator is currently in a closed state.

5. The augmented reality based method for monitoring safety of the carbon dioxide incubator according to claim 1, wherein the method for constructing the matrix of the carbon dioxide incubator in the real coordinate system comprises: configuring a plurality of markers on the carbon dioxide incubator; installing a camera, the installed camera being capable of identifying all of configured markers; setting a coordinate system from camera's perspective; and calculating coordinates of all markers under a coordinate system from camera's perspective, for tracking a position of the carbon dioxide incubator with the markers.

6. The augmented reality based method for monitoring safety of the carbon dioxide incubator according to claim 1, wherein a method for the constructing the matrix of the carbon dioxide incubator in the virtual coordinate system comprises: rendering a template image, setting a virtual marker information on the template image, establishing a virtual space coordinate system according to the rendered template image, and calculating marker coordinates in a virtual template image according to the virtual space coordinate system.

7. The augmented reality based method for monitoring safety of the carbon dioxide incubator according to claim 1, wherein the method for transforming the matrix in the real space coordinate system into the matrix in the virtual coordinate system comprises: identifying an identification information of a virtual template image, taking the identification information as a feature point, performing feature comparison between the feature point and the identification information in the real space coordinate system, obtaining a matrix in the real coordinate system of the matched identification information in real coordinate system, calculating a coordinate system transformation matrix after the feature comparison, and combining a real image of the carbon dioxide incubator with the virtual template image according to the transformation matrix.

8. An augmented reality based system for monitoring safety of the carbon dioxide incubator, wherein the system implements the augmented reality based method for monitoring safety of a carbon dioxide incubator according to claim 1.

9. A non-transitory computer-readable storage medium, wherein the computer-readable storage medium stores a computer program, and the computer program can be executed by a processor to implement the augmented reality based method for monitoring safety of a carbon dioxide incubator according to claim 1.

* * * * *